United States Patent [19]

Seger et al.

[11] 4,188,267
[45] Feb. 12, 1980

[54] METHOD AND APPARATUS FOR MEASURING THE INTEGRITY OF AN ELECTROLYTIC CELL LINING

[75] Inventors: Edward J. Seger, Apollo; Warren E. Haupin, New Kensington, both of Pa.

[73] Assignee: Aluminum Company of America, Pittsburgh, Pa.

[21] Appl. No.: 913,604

[22] Filed: Jun. 8, 1978

Related U.S. Application Data

[63] Continuation-in-part of Ser. No. 797,748, May 17, 1977, abandoned.

[51] Int. Cl.² ............................................. G01N 27/46
[52] U.S. Cl. ...................................... 204/1 T; 204/95; 204/195 R; 204/243 R; 324/51
[58] Field of Search ................. 204/1 T, 1 R, 195 R; 324/51

[56] References Cited

U.S. PATENT DOCUMENTS

| | | | |
|---|---|---|---|
| 2,858,507 | 10/1958 | Liautaud et al. | 324/51 |
| 3,141,128 | 7/1964 | Behr | 324/51 |
| 3,406,103 | 10/1968 | Raetzsch | 204/1 T |
| 3,648,163 | 3/1972 | Pinner et al. | 324/51 |
| 3,661,748 | 5/1972 | Blackmer | 204/1 T |
| 3,718,568 | 2/1973 | Neuwelt | 204/1 T |
| 3,773,643 | 11/1973 | Russel et al. | 204/243 R |
| 3,779,699 | 12/1973 | Russell et al. | 204/243 R |

Primary Examiner—T. Tung
Attorney, Agent, or Firm—Glenn E. Klepac; Elroy Strickland

[57] ABSTRACT

A method of operating an electrolytic cell having a corrosive environment. For electrolytic operation, the cell is supplied with DC current from current carrying buses or leads located externally of the cell. AC voltage is applied between the shell and at least one of the buses, and an AC meter is electrically connected between the bus and the shell for continuously monitoring the level of electrical resistance existing between the bus and the shell. The resistance monitoring determines the existence of any leakage current flowing between the bus and the shell, which is, in turn, an indication of the quality of the insulating wall of the cell.

2 Claims, 1 Drawing Figure

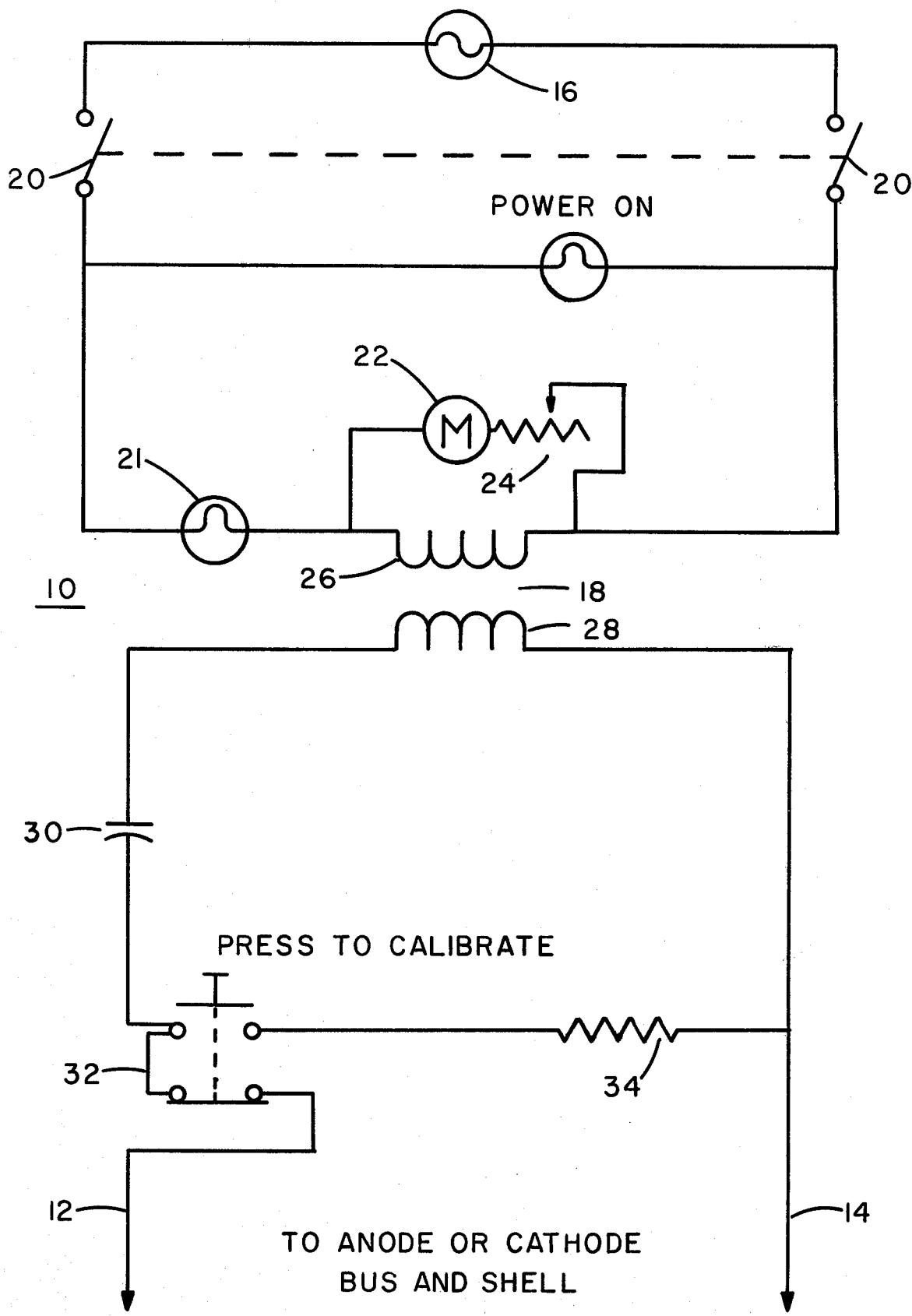

METHOD AND APPARATUS FOR MEASURING THE INTEGRITY OF AN ELECTROLYTIC CELL LINING

CROSS REFERENCE TO RELATED APPLICATION

This application is a continuation-in-part of Edward J. Seger et al U.S. Ser. No. 797,748, filed May 17, 1977, now abandoned.

BACKGROUND OF THE INVENTION

The present invention relates generally to the operation of an electrolytic cell, and particularly to a method that permits continuous monitoring of leakage current between electrical leads of the cell and an outer metal shell of the cell.

Electrolytic cells having a corrosive environment are generally provided with an interior lining of corrosion and heat resistant, insulating materials, these materials being contained in an outer structural shell of a material such as steel. In the operation of such cells there is always the danger that constituents of the corrosive environment will enter cracks, breaks or pores of the insulating materials, and thereby reach the metal shell, as explained, for example, in U.S. Pat. Nos. 3,773,643 and 3,779,699 to Russell and Knapp. Upon reaching the shell, the constituents corrode and eventually eat through the shell. Incipient conditions of this kind can be determined by measuring DC current between the shell and the bus or lead supplying current to or removing current from the cell, for example as shown in U.S. Pat. No. 3,406,103 issued in the name of Carl W. Raetzsch. However, continuous DC measurements have certain detrimental effects in the operation of the cell. In the case of cells designed to produce aluminum by electrolysis in a bath of molten salt, continuously monitoring DC current between the shell and a current carrying conductor connected to the cell causes stringers or fingers of aluminum metal to grow inwardly from the shell if the shell is made cathodic by the monitoring process and apparatus, and outwardly from the cathode if the shell is anodic. This, of course, increases leakage current, as the metal of the stringers is much more effective in conducting electrical current than the corrosive constituents creating the original problem. In order to avoid such stringer growth, only periodic DC measurements can be taken, with the time between these measurements affording opportunity for further corrosive attack on the shell to go unnoticed and unmonitored.

As further indicated in the above Russell and Knapp patents, if the cell shell becomes anodic nascent chlorine is produced on the surface of the shell which quickly eats away and perforates the shell. Thus, a DC connection that renders the shell anodic is to be avoided also.

Another disadvantage in using DC measurements to determine the existence of fluid leaks in a cell lining is that the accuracy of such DC measurements is adversely affected by the electrochemical phenomenon of electrolysis that occurs within the operating cell. This is a DC phenomenon which is generally not constant, as conditions within the cell change due to the continuous decomposition of the materials employed in the process, which are in turn being continually replenished by additions of the materials to the cell. Such changing conditions will be reflected in any DC measurement taken between the shell and the cell bus.

BRIEF SUMMARY OF THE INVENTION

The present invention is directed to the application of an AC voltage between the metal shell of an operating cell and an associated current carrying bus, and continuously monitoring any AC current that may be flowing between the bus and the shell. This is accomplished by an AC meter connected between the bus and the shell. If no AC current is flowing between the bus and the shell, the meter is adapted to read an infinite, or at least a large, electrical resistance to indicate an ideal leakage current condition, i.e., the shell is clearly electrically insulated from the bath of the cell and from the electrical leads extending through the shell and insulating cell wall. However, if the condition of the insulating walls of the cell or the insulating sleeves surrounding the electrical leads to the cell are such that corrosive constituents are penetrating to the shell, an AC leakage current will flow between the bus and the shell to be indicated by the meter.

With such a monitoring arrangement no DC connection is made between the bus and the shell to cause formation of chlorine or metal stringers, and the accuracy of the AC reading is not affected by the DC electrolytic action of the cell.

BRIEF DESCRIPTION OF THE DRAWING

The invention, along with its objectives and advantages, will best be understood from consideration of the following detailed description and the accompanying drawing, the sole FIGURE of which is a schematic circuit diagram of a preferred embodiment of the invention.

DETAILED DESCRIPTION OF PREFERRED EMBODIMENT

In reference to the sole FIGURE, a circuit arrangement 10 is shown for applying low voltage (six volts, for example), alternating current between the shell of a cell (not shown) and the anode or cathode bus (not shown) connecting the cell to a source of DC current (not shown). The low AC voltage is applied through leads 12 and 14, as schematically represented in the FIGURE. The arrangement 10 requires a primary source of AC current 16, such as the ordinary 120-volt house current, connected across a transformer 18 through a single throw line switch 20 and a light bulb 21 of low wattage (on the order of fifteen watts, for example). Transformer 18 may be the type of transformer known as a filament voltage transformer, though the invention is not limited thereto. A "filament" transformer takes its name from the practice of supplying the filaments of vacuum tubes used in radios and television receivers with 6.3 volts. This voltage was developed across the low voltage, secondary winding of a transformer, the primary winding of the transformer being connectable across a source of 120 volts of alternating current which is the common house current.

A meter 22 and a potentiometer or rheostat 24, connected in electrical series, are connected across the high voltage, primary side of transformer 18, i.e. across primary winding 26, while the low voltage side and winding 28 of 18 is connected to leads 12 and 14, and thus to a cell shell and bus (not shown). An AC capacitor 30 and a double throw, double pole switch 32 are shown serially connected in the line of lead 12. Capacitor 30 may be an AC motor starting capacitor; a capacitance of 3900 mfd has been found suitable for the purposes of the invention.

In the operation of circuit 10, with the closing of switch 20, the voltage of AC source 16 appears across winding 26 of transformer 18. The voltage drop across the light bulb 21 is negligible because of the absence of significant current flow in the circuit of 26. A full scale movement of meter 22 is then adjusted, via potentiometer 24, to read a major portion of the voltage of 16. For example, if the voltage of 16 is 120 volts, meter 22 can be adjusted to read 100 volts full scale, the remaining 20 volts on the primary winding appearing across the potentiometer. With the voltage of 16 applied across the primary winding, meter 22 measures this voltage with exception of that appearing across 24.

With the low voltage winding 28 of the transformer connected between the shell of an electrolytic cell and an associated cathode or anode bus (by leads 12 and 14), any leakage current flowing between the shell and the bus will appear across low voltage winding 28. This AC leakage current is induced in primary winding 26 such that current now also flows in the circuit of the primary winding, which circuit includes light bulb 21. Current flow through the filament of the bulb causes a voltage drop to occur across the filament, which voltage drop reduces the voltage appearing across transformer winding 26. Meter 22 now reads this voltage as an indication of the amount of leakage current. This amount is preferably read in terms of electrical resistance (ohms), i.e., the face of the meter is changed from that of a voltage scale to that of an electrical resistance scale. In addition, the scale is preferably made non-linear in a manner that spreads apart the low resistance end of the scale to permit easier and more accurate viewing of low resistance readings.

In addition to the reading provided by meter 22, the current flow through bulb 21 causes the filament thereof to glow (or glow brighter), which provides another indication of leakage current in amounts that signal a critical insulating condition in the cell wall.

Light bulb 21, with a tungsten filament, for example, serves also as a current regulator in the primary circuit of transformer 18, as the electrical resistance of tungsten metal is proportional to its temperature. An increase in current flow through the filament increases its temperature, which in turn, increases the resistance of the filament to current flow, thereby inherently stabilizing current flow. The opposite phenomenon occurs with a decrease in the flow of current through the filament.

With little or no leakage current flowing between the shell of a cell and an associated current carrying lead or bus, little or no current is induced in primary winding 26 from secondary winding 28 (of 18) to cause a change in the voltage appearing across 26 and meter 22.

Switch 32 and a resistor 34 are provided in the circuit of 10 as a means to calibrate meter 22. 32 is a double pole, double throw switch that is effective to open the circuit of lead 12 while closing the circuit of resistor 34 to place the same in series with transformer winding 28. The opening of the circuit 12 isolates meter circuit 10 from the cell or bus so that meter 22 reads only the resistance of 34. The resistance of 34 is low, on the order of four ohms, for example, to insure calibration of the meter in the range of criticality, i.e., in the range of resistance in which cell insulation has deteriorated to the degree that a substantial amount of current is allowed to flow between the interior of the cell and the shell of the cell. The alternating voltage applied across primary winding 26 from source 16 induces an amount of current in the circuit of secondary winding 28 sufficient to provide a reading of the resistance of 34 to the flow of the current, i.e. transformer 18, in reducing the voltage to secondary winding 28, increases the current flow in 28 by a corresponding amount.

After the meter is calibrated, switch 32 is reset to disconnect resistor 34 and to reconnect lead 12 and the meter circuit to the operating cell.

While the invention has been described in terms of preferred embodiments, the claims appended hereto are intended to encompass all embodiments which fall within the spirit of the invention.

What is claimed is:

1. A method for continuously electrically monitoring the integrity of a lining in an electrolytic cell having an outer metal shell and a lining within said shell containing a corrosive environment, said cell being supplied with DC current by lead members extending through said shell from buses located externally of the cell, the method comprising the steps of connecting the primary winding of a filament type transformer to a source of house voltage, connecting the secondary of the transformer between at least one of said buses and the shell, such that an AC voltage of a house frequency is applied between the bus and shell, and continuously monitoring the existence of any AC leakage current flowing between the bus and shell through the use of an AC voltmeter connected across the primary winding of the transformer and having a scale providing readings in electrical resistance, said leakage current being indicative of the electrical resistance condition existing between the one bus and the shell.

2. In an electrolytic cell including an outer metal shell, a lining within said shell containing a corrosive environment, a plurality of buses located externally of said shell, and a plurality of lead members extending through the shell from the buses for supplying DC current to the cell, the combination with said cell of means for continuously electrically monitoring the integrity of said lining without degrading the cell electrolytically, comprising (a) a low voltage AC circuit for applying alternating current between the shell and one of said buses;
(b) a high voltage AC circuit;
(c) a transformer connecting the low voltage AC circuit to the high voltage AC circuit and including a low voltage winding in the low voltage AC circuit and a high voltage winding in the high voltage AC circuit; and
(d) an AC voltmeter providing readings of electrical resistance connected across the high voltage winding of the transformer for measuring voltage drop across said high voltage winding as an indication of resistance in the low voltage AC circuit.

* * * * *